United States Patent [19]

Markowitz et al.

[11] Patent Number: 5,273,035
[45] Date of Patent: Dec. 28, 1993

[54] DUAL CHAMBER PACEMAKER WITH SAFE ATRIAL PACING

[75] Inventors: H. Toby Markowitz, Roseville; John C. Stroebel, Blaine; Robert A. Betzold, Fridley, all of Minn.

[73] Assignee: Medtronic, Inc., Minneapolis, Minn.

[21] Appl. No.: 829,811

[22] Filed: Feb. 3, 1992

[51] Int. Cl.⁵ .......................................... A61N 1/362
[52] U.S. Cl. .................................................. 607/14
[58] Field of Search ............................ 128/419 PG

[56] References Cited

U.S. PATENT DOCUMENTS 4,951,667 8/1990 Markowitz .................. 128/419 PG
5,027,815 7/1991 Funke ............................ 128/419 PG

OTHER PUBLICATIONS

Copy of the disclosure by Dr. Den Dulk.

Primary Examiner—William E. Kamm
Assistant Examiner—Scott M. Getzow
Attorney, Agent, or Firm—Reed A. Duthler; Harold R. Patton

[57] ABSTRACT

A dual chamber pacemaker is provided, preferably either DDDR or DDIR, having logic hardware and/or software for normally carrying out the DDIR or DDDR mode of operation, and further having means for carrying out a safe atrial pace method of operation in circumstances where normal atrial pacing could otherwise be competitive or result in loss of atrial capture. The pacemaker has means for detecting an atrial sense during PVARP, timing out a delay from the time of the early atrial sense, delivering a safe atrial pulse at the end of the delay, and controlling generation of a ventricular pace pulse in synchronous relation to the safe atrial pulse and with at least a minimum AV interval.

22 Claims, 6 Drawing Sheets

DUAL CHAMBER PACEMAKER WITH SAFE AIRIAL PACING

CROSS REFERENCE TO CO-PENDING APPLICATION

Reference is made to U.S. patent application Ser. No. 07/830,089, by Den Dulk, filed as of the date of the present application.

BACKGROUND OF THE INVENTION

1. Field of the Invention

This invention relates to cardiac pacemakers and, more particularly, to a dual chamber pacemaker and method of pacing which optimizes pacemaker response to an early sensed atrial beat.

2. Description of the Prior Art

Various types of pacemakers are disclosed in the prior art, and are presently in widespread use. The pacing literature has documented the different types of pacemakers and their characteristics extensively. An excellent summary of the evolution and characteristics of pacemaker types, and specifically different types of dual chamber pacemakers, is set forth in U.S. Pat. No. 4,951,667, Markowitz et al., which is incorporated herein by reference.

Another and more recent advance in the field of cardiac pacing systems is that of the rate responsive pacemaker which increases cardiac output in response to exercise or other body demands. Such pacemakers may control pacing rate based upon sensing any one or a combination of different body parameters such as body activity, blood pH, respiratory rate, QT interval or historical atrial activity. See, for example, U.S. Pat. No. 4,428,378, Anderson et al., disclosing a pacemaker which varies pacing rate in response to sensed patient activity; and U.S. Pat. No. 4,228,308, Rickards, which discloses controlling pacing rate in response to Q-T interval. Additionally, rate responsive control has been integrated into dual chamber pacing systems, e.g., DDDR and DDIR systems. See "Rate Responsive Dual Chamber Pacing" in *PACE*, vol. 9, pp. 987-991; U.S. Pat. No. 4,467,807, Bornzin; and the above-noted U.S. Pat. No. 4,951,667.

A problem that has been recognized as arising in dual chamber pacemakers is that of "competitive atrial pacing" where, following an early natural atrial depolarization, the pacemaker may either fail to achieve atrial capture with a subsequent atrial pace pulse, or the atrial pace pulse may induce an atrial arrhythmia. Dual chamber pacing at rapid rates implies pacing near and possibly within the atrial cardiac refractory period of spontaneous P-waves, PACs and retrograde P waves. If atrial pacing occurs within the natural refractory period of the atrium, i.e., the refractory period of the heart, not that of the pacemaker, the pace stimulus will not capture the atrium. In such a situation, the actual interval between atrial and ventricular depolarizations will be prolonged beyond the physician-programmed AV interval. Further, if atrial stimuli are delivered such that they fall not in the natural refractory period of the atrium, but immediately afterwards, there exists the potential to initiate atrial fibrillation, atrial flutter, or other re-entrant tachycardias. This likelihood is especially prevalent in patients with a prior history of atrial arrhythmias. One prior art response to the detection of a PAC is to switch the mode of the dual chamber pacemaker into a ventricular asynchronous mode of operation, i.e., sacrifice synchronous operation and simply deliver ventricular pace pulses at a fixed rate until natural atrial signals are sensed having timing which enables switching back to synchronous operation. See, for example, the patent to Funke et al., U.S. Pat. No. 5,027,815, also incorporated herein by reference, where the response to an early atrial sense is to simply inhibit delivery of an atrial pulse and proceed to deliver the ventricular pulse at the scheduled time. In this type of dual chamber system, ventricular rate regularity is maintained, but at the expense of synchronous pacing operation.

The consequence of either switching to asynchronous operation, or pacing the atrium at a time which causes loss of atrial capture with a resultant long AV interval, has the adverse effect of hemodynamic loss of the atrial kick on ventricular filling, and decrease in subsequent cardiac output. Also, a long interval between atrial and ventricular depolarizations allows the normal AV conduction system to repolarize and conduct retrogradely to the atrium. In this manner, the patient may suffer from the contraction of the atria on closed AV valves (i.e., the pacemaker syndrome) and even worse, the patient may be subject to initiation of pacemaker-mediated tachycardia (PMT). Maintaining short or reasonable AV intervals is critical to prevention of PMT.

A response to these concerns is found in the patent to Markowitz et al., U.S. Pat. No. 4,951,667, incorporated herein by reference. The pacemaker of this patent responds to an atrial sense (AS) that is deemed early by delaying the timing of the atrial pulse (AP) which is to be delivered, to correspond to a lower pacing rate. The scheduled VA interval is normally set by a sensor, i.e., it is a rate responsive interval. When and if a natural atrial signal is sensed within a relative atrial refractory period, and also within a safety period just preceding the time out of the scheduled VA escape interval, then the VA interval is shifted to a longer interval corresponding to a lower rate. Thus, instead of delivering an atrial pulse at the normal scheduled time, it is delayed following such an early atrial sense, and the ventricular pace pulse (VP) is synchronized to the delayed atrial pace pulse. However, while this arrangement increases the probability of safe atrial pacing, there is no mechanism for ensuring that the atrial pacing pulse will be delivered at least a safe interval following the early atrial depolarization. Further, the atrial pace pulse is not correlated to the early atrial sense, such that the ventricular pace rate can vary widely, from a relatively high rate to a low rate.

There thus remains a need for a pacemaker, and method of pacing which maintains safe synchronized dual chamber pacing wherever possible. It is undesirable from both hemodynamic and electrophysiologic rationales to allow atrial pacing during times at which the pacemaker may either fail to capture or may induce an arrhythmia. It is the intention of the safe atrial pacing feature of this invention to reduce the occurrence of such behavior, and to the full extent possible eliminate it, i.e., avoid competitive atrial pacing while maintaining synchronous pacing.

SUMMARY OF THE INVENTION

It is an object of this invention to provide a method of dual chamber pacing, and a pacemaker for such pacing, which responds to sensed early atrial signals in a way such as to avoid atrial competition, while at the same time optimizing dual chamber synchronous operation and minimizing ventricular rate variation.

In accordance with this object, there is provided a dual chamber pacemaker having means for identifying sensed early atrial signals with respect to which scheduled atrial pulses would be potentially competitive. The pacemaker has means for timing a delay from the time of the early atrial sense and for controlling delivery of an atrial pulse at the end of the delay rather than at the end of the prior scheduled atrial escape interval. The pacemaker controls the generation of a ventricular pace stimulus in synchronous relation to the delayed atrial pace stimulus, and minimizes the AV delay in a way such as to maintain effective synchrony while minimizing variation in ventricular rate.

DESCRIPTION OF THE PREFERRED EMBODIMENTS

The following symbols are used in the specification to define events, intervals, and times:

| AS | atrial sense |
|---|---|
| ASR | atrial sense during PVARP |
| AP | atrial pace |
| SAP | safe atrial pace |
| VP | ventricular pace |
| EI | escape interval |
| $VA_{ei}$ | atrial escape interval, illustrated as the interval from V event to scheduled delivery of an AP |
| $VV_{ei}$ | ventricular escape interval, illustrated as the interval from V event to scheduled delivery of a VP assuming an AP occurs. |
| AIW | interval timed out after an early atrial sense, and representing period of vulnerability or inexcitability of the atrium |
| $t_w$ | time when AIW ends |
| $AV_{min}$ | the minimum AV interval during safe atrial pacing operation to which the AV interval may be compressed |
| $t_{VA}$ | time when $VA_{ei}$ ends |
| $t_{VV}$ | time when $VV_{ei}$ ends |
| $t_{AS}$ | time of early atrial sense |
| DDD? | DDD or DDDR mode |
| DDI? | DDI or DDIR mode |
| PVARP | post-ventricular atrial refractory period |
| PVAB | post-ventricular atrial blanking |
| PAV | paced AV interval, i.e., AV interval to follow atrial pacing |
| SAV | sensed atrial interval, i.e., AV interval to follow sensed atrial beat |

In the following discussion, the pacemaker is illustrated as being ventricular-time-based, i.e., timing is referenced to the ventricular event. It is to be noted that atrial, or A-A timing is equally suitable for this invention. Thus, e.g., the atrial escape interval may be the V-A time, or the A-A time; the ventricular escape interval may be calculated as V-A interval plus PAV interval, etc. V-A timing is used consistently for purposes of illustrating the timing of the invention.

Figure 1:
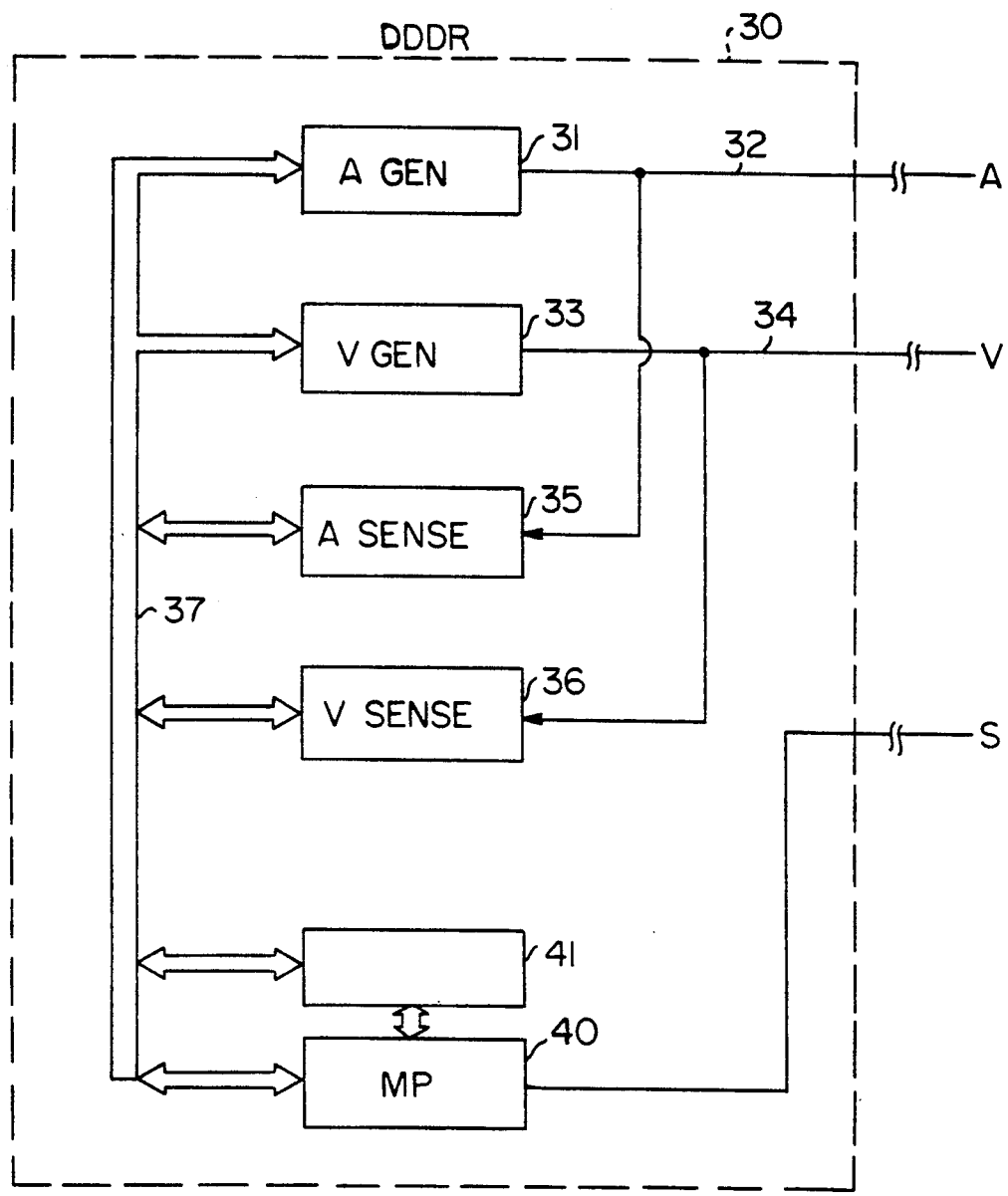
FIG. 1 is an illustrative block diagram of the components of the dual chamber pacemaker system as utilized by this invention, showing the relationship of the control unit to the primary signal sensing and stimulus generating elements.

Referring now to FIG. 1, there is shown a basic block diagram of the primary hardware components of a DDR pacer 30, it being noted that the invention is also applicable to other types, e.g., DDI, DDIR and DDD. In DDI and DDD type pacers, the safe atrial pacing feature will primarily be of benefit in those cases in which variable V-A intervals are provided, e.g., in pacers which employ flywheel pacing, rate smoothing, or other similar features, or when the rate is programmed to a high value (i.e., >1006 pm).

An atrial pace pulse generator 31 is shown, which is connected to the patient's atrium through lead 32, for delivery of pacing pulses. An A sense amplifier 35 is illustrated, also connected to atrial lead 32, to receive and sense signals from the patient's atrium. A ventricular pace pulse generator 33 is illustrated which is connected to the patient's ventricle through lead 34, to deliver pacing pulses, and V sense amplifier 36 is also connected to lead 34, to receive and sense signals from the patient's ventricle. Generators 31 and 33, and sense amplifies 35 and 36, are interconnected with microprocessor 40, and/or other desired control hardware 41, for control of timing of pulse delivery, blanking, refractory intervals, and the like, in a well known matter. Microprocessor 40 suitably has software which is parameter-driven to control the operation of the hardware units. Such software control is well known in the art, and has been incorporated into both external and implantable commercial pacemakers. As affects the scope of this invention, the degree to which software supplants hardware, or vice-versa, is a matter of design choice. Thus, for the timing functions that are carried out in the pacing system of this invention, it is to be understood that the microprocessor may have built-in timing circuits, or suitably may control external hardware timer circuits. Software control of pacing functions is well known in the art, such that the following detailed discussions of the timing and software specifications enable one of ordinary skill in this art area to design a system for carrying out the required functions within the scope of the invention.

A sensor S is illustrated as providing an input to the microprocessor 40. Sensor S is understood to be representative of any type of sensor, or combination of sensors, as known in the pacer art for developing one or more signals from which a desired sensor pacing rate can be developed. Although the sensor S is illustrated as being outside of the pacemaker 30, it can be positioned within or without the pacemaker housing. Likewise, a body parameter representative of desired pacing rate may be derived from one or both of the pacing leads, e.g., the QT pacemaker of the above-noted U.S. Pat. No. 4,228,803. A DDDR pacemaker also has hardware and/or software for transforming the sensed signal or signals into a desired sensor rate control signal, for controlling pacing rate, in a known fashion.

Figure 2A:
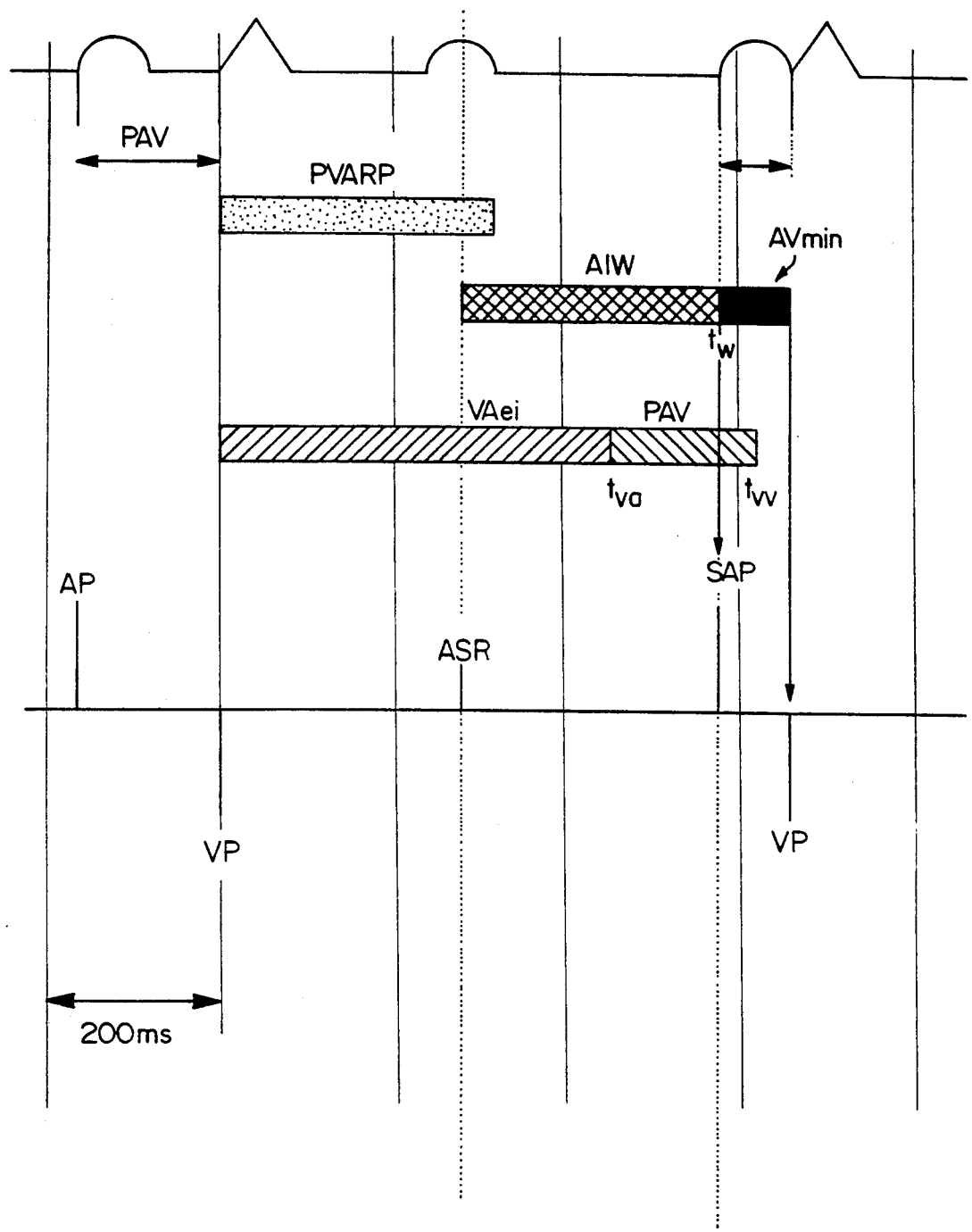
FIG. 2(a) is a series o timing diagrams illustrating atrial and ventricular events and pacemaker time periods, for an illustrative situation where an early atrial sense results in a safe atrial pace and a ventricular pace which is delivered following an AV delay of $AV_{min}$.

FIG. 2(a) illustrates the timing of this invention, by which the pacemaker responds to an early atrial sense (ASR) so as to avoid competitive atrial pacing, but yet maintains consistent AV synchronous operation. The top diagram of FIG. 2(a) represents an EKG, illustrating both atrial and ventricular events and pacemaker spikes; the bottom diagram represents a marker channel, and the middle three diagrams represent pacemaker time periods, as labelled. A first pair of atrial and ventricular pace pulses is shown, separated by the normal AV interval (PAV). Beginning with the ventricular pace pulse, a post ventricular atrial refractory period (PVARP) is timed. As used in this specification, the term PVARP may comprise PVAB, during which the atrial sense amplifier is blanked. PVARP refers to an atrial sense period following a ventricular event during which a sensed atrial signal is not used to initiate an AV interval (SAV). By contrast, any atrial sense after the end of PVARP, and up to the end of the scheduled VA interval (the VA interval is illustrated as $VA_{ei}$) is used to initiate an SAV interval, the time out of which can trigger a synchronized ventricular pulse. Thus, PVARP may be any portion of the post-ventricular period up to the time when the occurrence of an AS initiates timing of an AV delay for ventricular tracking of the atrium.

Still referring to FIG. 2(a), and remembering that the invention is illustrated by V-V timing, the control circuitry of this invention normally times a scheduled VA interval ($VA_{ei}$), referred to as the atrial escape interval, and ending at $t_{VA}$. The end of $VA_{ei}$ is followed by a scheduled PAV, which ends at tvv ($VA_{ei}$ and PAV make up the ventricular escape interval). Also, although not illustrated, if an AS appears after PVARP, the pacer times a normal AV interval (SAV) and delivers at the end of SAV a synchronized ventricular pulse in the absence of an intervening VS. Note that these intervals may vary, e.g., in a rate responsive mode or as illustrated in the Funke et al. U.S. Pat. No. 5,027,815. However, if an atrial sense is recognized within the effective PVARP, as illustrated, then a time interval AIW is timed out commencing with the early sense (ASR). When this happens, delivery of an AP at the end of $VA_{ei}$ is inhibited, and a safe atrial pulse is generated and delivered at the end of AIW ($t_w$). An AV interval which is shorter than PAV and greater than or equal to $AV_{min}$ is initiated, resulting in delivery of a ventricular stimulus at the conclusion thereof. In a typical embodiment, AIW may be 300 ms, and $AV_{min}$ is 80 ms. These figures are, of course, illustrative, and other values may be selected for use in this invention.

Figure 2B:
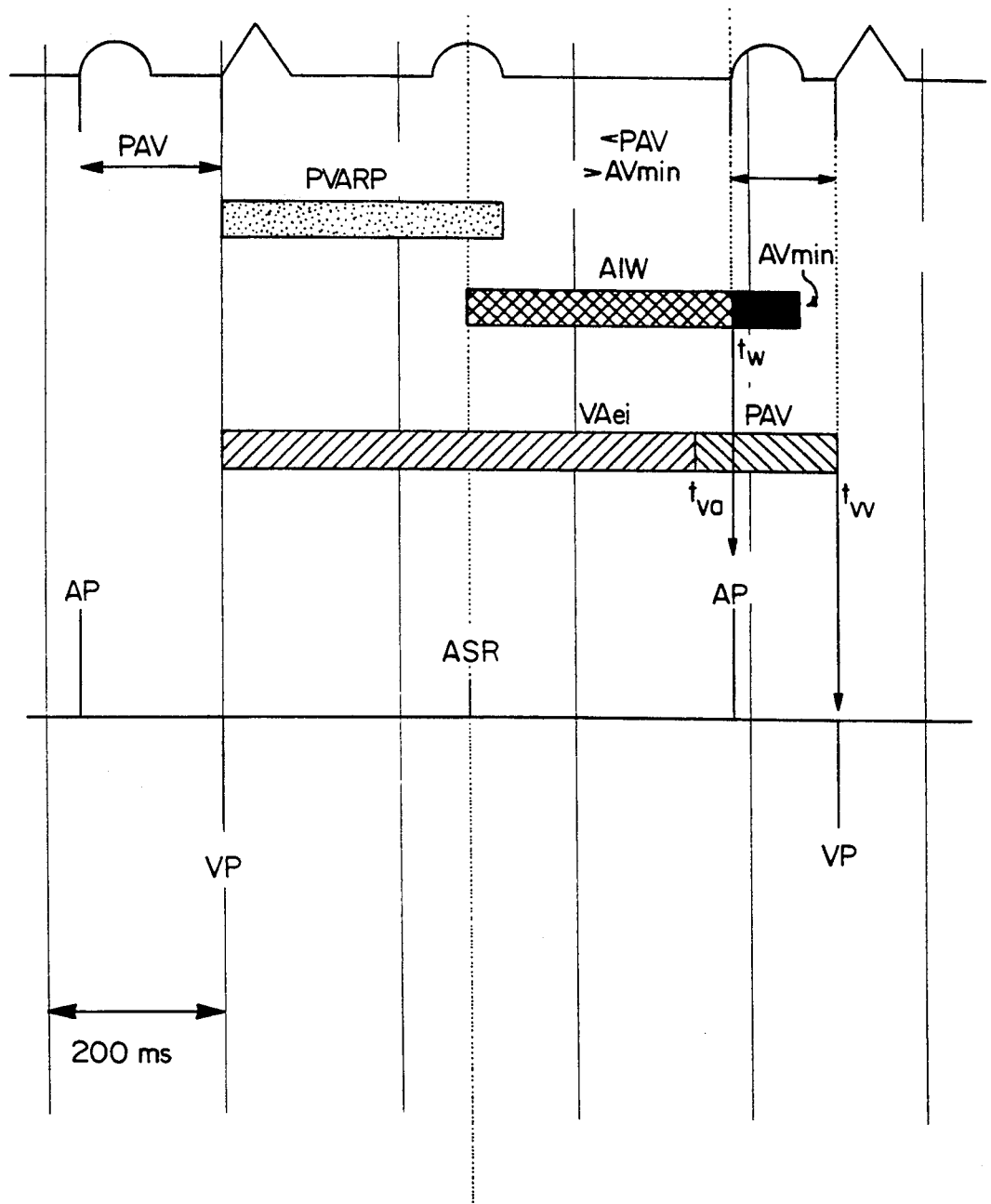
FIG. 2(b) is a series of timing diagrams illustrating atrial and ventricular events and pacemaker time periods, for an illustrative situation where an early atrial sense results in a safe atrial pace and a ventricular pace which is delivered following a compressed AV delay which is less than the scheduled PAV but greater than $AV_{min}$.

As illustrated in FIG. 2(a), where the end of AIW ($t_w$) occurs after the calculated end of $VA_{ei}$ ($t_{VA}$), the shortened AV interval results in the ventricular pace being delivered close to the scheduled $t_{VV}$, i.e., the change in Ventricular pacing rate is small. Note, however, that there is a limit to how much the AV interval can be shortened and still maintain effective synchrony, and for this reason a condition is imposed that the AV delay following a SAP must be at least as great as $AV_{min}$, which can be programmed by the physician. Note, however, that the AV delay following an SAP can be as long as the scheduled PAV. FIG. 2(b) illustrates the same situation as FIG. 2(a), except that $VA_{ei}$ has been extended from about 450 ms to 550 ms (as seen by comparing $VA_{ei}$ to the 200 ms reference). This results in the calculated $t_{VV}$($VA_{ei}$+PAV) being later than the end of AIW+$AV_{min}$, in which case the later time is chosen to schedule delivery of ventricular pace in order to optimize AV synchrony and maintain regularity of the ventricular rhythm. Thus, as seen also in connection with FIGS. 3(a) and 3(b), the logic is to choose the later of $VA_{ei}$+PAV, or AIW+$AV_{min}$.

Figure 2C:
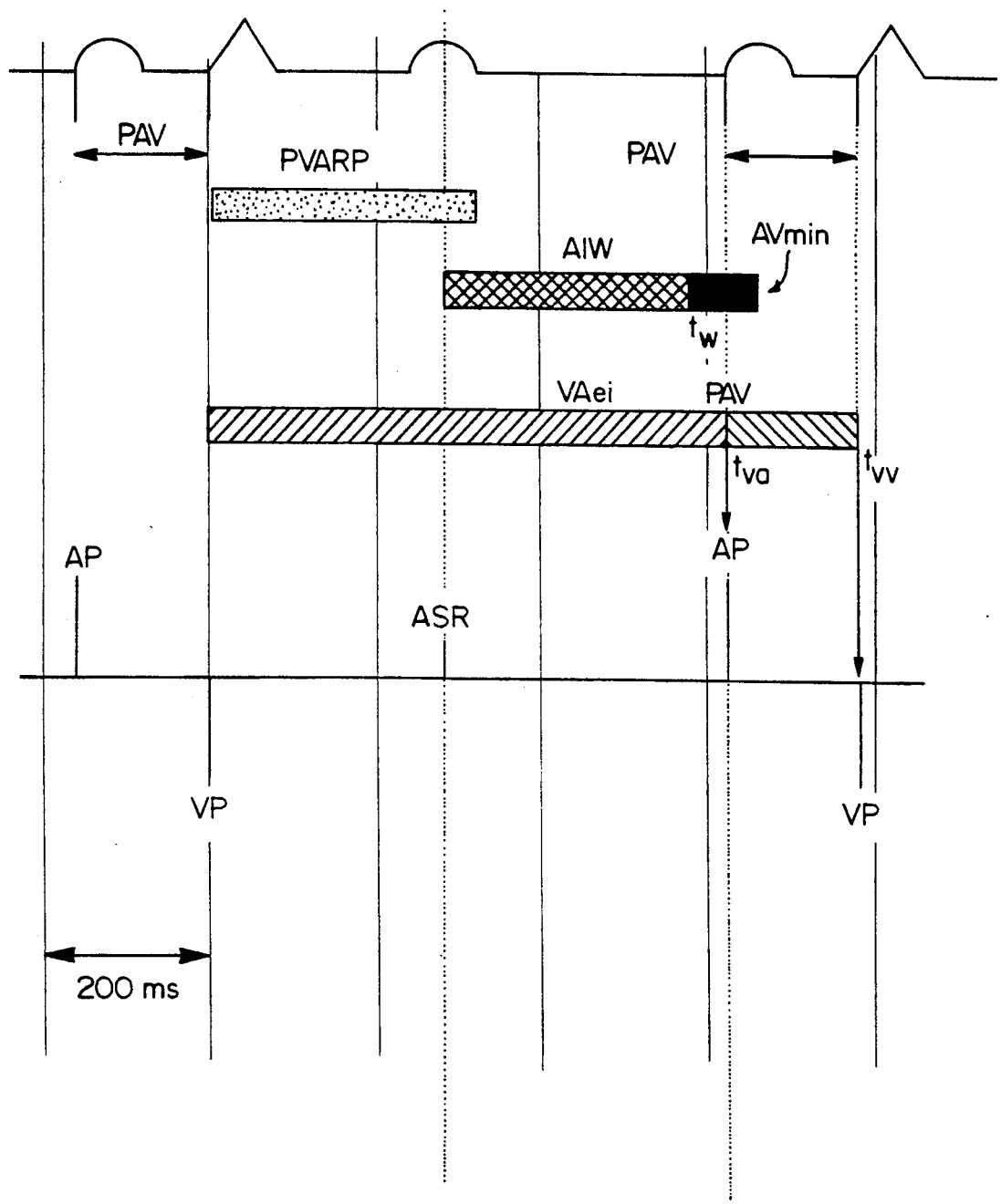
FIG. 2(c) is a series of timing diagrams illustrating atrial and ventricular events and pacemaker time periods, for an illustrative situation where an early atrial sense does not alter the scheduled delivery of atrial and ventricular paces.

FIG. 2(c) illustrates the situation where $VA_{ei}$ is even larger (about 625 ms), such as where the sensor calls for a lower pacing rate. Here, $t_w$ is calculated to occur before the end of $VA_{ei}$ ($t_{VA}$) In such a situation, the normally scheduled escape intervals can be maintained, so that there is no SAP delivered and the AP is delivered at scheduled $t_{VA}$. Thus, with this timing, the early atrial sense does not alter the standard DDDR or DDIR operation.

The following logical rules apply to safe atrial pacing in the DDI? and DDD? modes:

Upon an AS during PVARP, start the AIW interval.

Upon completion of the atrial escape interval ($VA_{ei}$), start the PAV interval;

if $VA_{ei}$ is completed during the ventricular refractory interval, cancel the AIW interval, and pace the atrium;

if $VA_{ei}$ is completed, not during the ventricular refractory period, not during the AIW interval, and the inhibit condition is false (no AS has occurred to inhibit delivery of an AP), pace the atrium.

Upon a further atrial sense not during PVARP, cancel the AIW interval, and if in DDI? mode: if during the atrial escape interval, declare the atrial inhibit condition; if not during the escape interval, and not during the PAV interval, pace the ventricle.

if in DDD? mode, start the SAV interval.

Upon an atrial pace, start the $AV_{min}$ interval.

Upon completion of the AIW interval, if the escape interval ($VA_{ei}$) has completed, pace the atrium.

Upon completion of the $AV_{min}$, but not during the PAV interval, pace the ventricle.

Upon completion of the PAV interval, not during the $AV_{min}$ interval, and not during the AIW interval, pace the ventricle.

Upon a ventricular pace, or a ventricular sense,
start the escape interval,
reset the inhibit condition,
cancel the $AV_{min}$ interval,
cancel the PAV interval, and
cancel the SAV interval.

It is to be noted that these logic rules are intended to operate in conjunction with established methods for dual chamber pacing. Conditions such as inhibition of ventricular pacing have not been included in these rules. Likewise, conditions for carrying out ventricular safety pacing (VSP) have not been included. VSP is used as a safety measure against cross-talk inhibition. In VSP operation, if the ventricular sense amplifier senses a signal within a predetermined time interval following an atrial pace, then a VP is delivered at the end of such predetermined interval. Although not illustrated in this specification, VSP may be included in a pacemaker according to this invention.

Figure 3A:
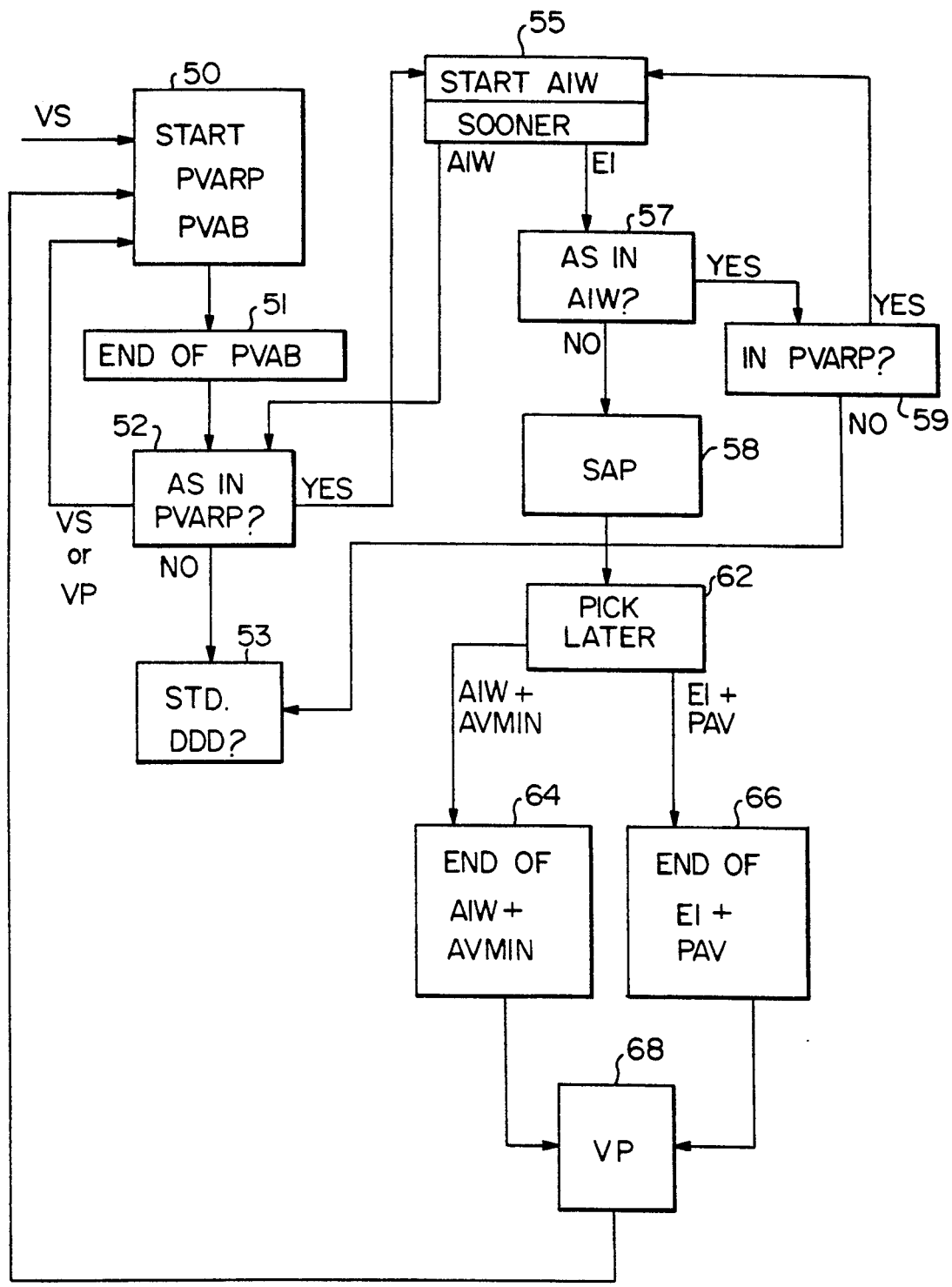
FIG. 3(a) is a flow chart showing the basic logic steps taken by hardware and/or software incorporated into a DDD or DDDR pacemaker of this system and adapted to carry out the logical operations to provide improved anti-competitive atrial pacing.

Referring now to FIG. 3(a), there is shown a flow diagram for carrying out the functions necessary for safe atrial pacing in the DDD? mode of a dual chamber pacemaker. As indicated at block 50, a ventricular event such as VS starts the timing of PVAB and PVARP. PVAB causes blanking of the atrial sense amplifier, and may be accomplished by any desired combination of hardware and software. At the end of PVAB, at block 52 it is determined whether an atrial sense occurs (AS) in PVARP. If no, meaning the PVARP is timed out without any atrial sense, the logic branches to block 53, where standard DDD? operation is continued. However, when an AS is sensed in PVARP, the logic branches to block 55, where the AIW timer is initiated. Following initiation of the AIW period, the pacemaker calculates whether AIW or EI (e.g., $VA_{ei}$) is going to time out sooner. If AIW is calculated to time out sooner, the logic reverts to block 52, to continue to determine whether another AS will be detected within PVARP. Note that, as discussed above in connection with FIGS. 2(a)-(c), if AIW is calculated to time out sooner, there is no reason to deviate from waiting for the end of the escape interval; if no additional AS is sensed, the pacemaker proceeds to normal DDD? operation.

If, at 55, it is determined that the end of the AIW window is to occur after the escape interval, the pacemaker waits until the end of AIW at 57 and if no AS occurred within AIW, and an SAP is delivered directly, as indicated at block 58. When an AS occurs during AIW, the pacemaker branches to block 59, to determine whether this AS has occurred in PVARP. If no, meaning that it was an AS after the end of PVARP, the pacemaker branches to standard DDD? operation, as indicated by the branch leading to block 53. If the answer at 59 is yes, meaning that a second ASR has occurred in PVARP, then the pacemaker returns to 55 to start a new AIW. This ensures that when an SAP is delivered, it is delayed by at least AIW following the last ASR. Optionally, blocks 57 and 59 may be omitted and the device may proceed directly to block 58, triggering delivery of an SAP.

Referring back to the delivery of an SAP at block 58, the pacemaker proceeds to block 62 to determine when a VP can be delivered. The pacemaker picks which comes later, the calculated $AIW + AV_{min}$, or $EI + PAV$. If the former, then at block 64 the pacemaker determines the end of $AIW + AV_{min}$, and initiates delivery of a VP as shown at block 68. If $EI + PAV$ is calculated to occur later than $AIW + AV_{min}$, then at block 66 the pacemaker determines the end of $EI + PAV$, and initiates VP as indicated at block 68.

Figure 3B:
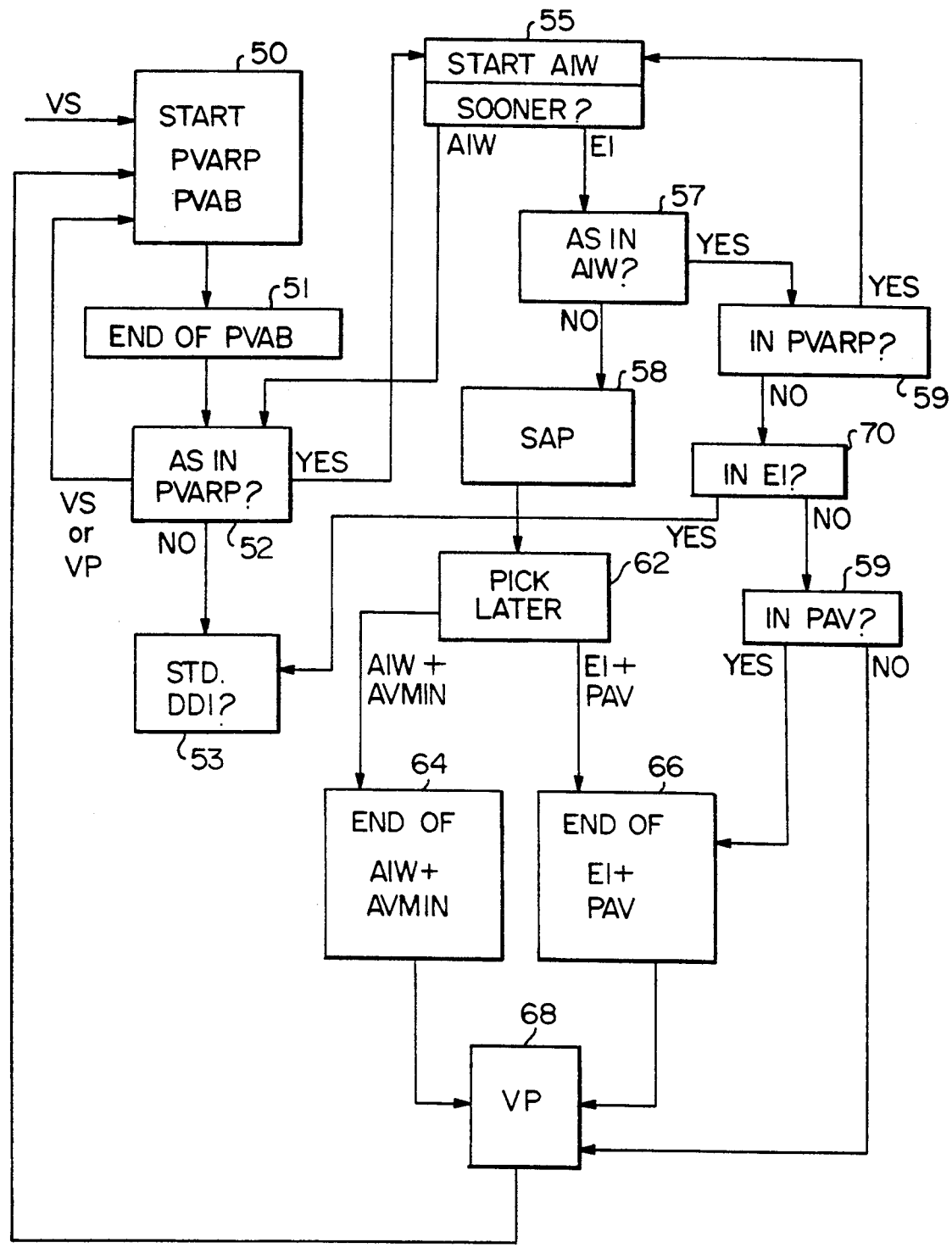
FIG. 3(b) is a flow chart showing the basic logic steps taken by hardware and/or software incorporated into a DDI or DDIR pacemaker of this system and adapted to carry out the logical operations to provide improved anti-competitive atrial pacing.

FIG. 3(b) is a modification of safe atrial pacing for the DDI? mode. In comparison to DDD? mode as indicated in FIG. 3(a), the difference is in the response following the detection of an AS in the AIW interval, but not in PVARP, as indicated at the "NO" output of block 59. At block 70, it is determined whether such AS occurred within EI. If yes, the pacemaker returns to standard DDI operation at block 53. If at block 70 the response is no, meaning that EI (e.g., $VA_{ei}$) has ended, the pacemaker goes to 72 where it is determined whether the AS has occurred in PAV. If yes, operation branches to 66, resulting in delivery of a VP at the end of $EI + PAV$. If no, a VP is delivered directly, or, alternatively, after a minimum A-V delay.

The system and method of this invention are seen to provide a response to sensed early atrial depolarizations in a manner that ensures avoidance of competitive pacing, and maintains atrial-ventricular synchrony when it paces the ventricle. This invention utilizes the rate responsive information available in a DDIR or DDDR pacer, by delivering the SAP directly upon completion of the AIW rather than waiting for the end of a low rate escape interval. By continuously searching for early atrial senses, the pacemaker is enabled to respond at times of greater risk, i.e., during periods of high rate response, while maintaining the benefits of rate responsiveness. Further, by compressing the following AV interval, a high degree of ventricular rate regularity is maintained along with continuous synchronous operation.

Although specific software embodiments have been presented, it is to be understood that the safe atrial pacing method of this invention can be carried out with somewhat different logical sequences, and in combination with other pacemaker functions.

What is claimed:

1. A dual chamber pacemaker having atrial sense means for sensing natural signals from a patient's atrium, ventricular sense means for sensing natural signals from said patient's ventricle, ventricular generator means for generating ventricular pace stimuli to be delivered to said patient's ventricle, atrial generator means for generating atrial pace stimuli to be delivered to said patient's atrium, rate control means for setting an atrial escape interval and for triggering generation of a said atrial pace stimulus at the expirations of said atrial escape interval, means for timing an AV interval and for triggering generation of a said ventricular pacing stimulus at the expiration of a said AV interval, and refractory means for normally timing an atrial refractory interval following ventricular pace stimuli, further comprising:

early sense means operative following ventricular pace stimuli for detecting an early atrial signal (ASR) that occurs during a said refractory interval, and for controlling the pacemaker response to any said ASR, said early sense means having inhibit means for timing a delay (AIW) from the time of said ASR and for inhibiting delivery of an atrial pulse during said AIW, atrial control means for controlling said atrial generator means to generate a delayed atrial pace stimulus (SAP) at the expiration of said AIW delay, whenever said AIW delay expires later than said atrial escape interval, and ventricular control means for controlling generation of a ventricular pace stimulus (VP) in synchronous relation to said delayed atrial stimulus, said ventricular control means comprising: means for defining a minimum interval following expiration of said AIW delay; and means responsive to the expiration of said AIW delay at a time greater than the duration of said minimum interval prior to the expiration of said atrial escape interval plus said AV interval for triggering delivery of a ventricular pacing stimulus at the expiration of said atrial escape interval plus said AV interval, and further responsive to the expiration of a said AIW at a time less than the duration of said minimum interval prior to the expiration of a said atrial escape interval plus said AV interval for triggering delivery of a ventricular pacing stimulus at the expiration of said minimum interval.

2. The dual chamber pacemaker as described in claim 1, wherein said pacemaker is a rate responsive pacemaker, and said rate control means has means for developing rate control signals representative of pacing rate and means for setting said atrial escape interval as a function of said rate control signals.

3. The dual chamber pacemaker as described in claim 1 wherein said minimum interval is shorter than AV interval.

4. The dual chamber pacemaker as described in claim 3, wherein said minimum interval is about 80 ms, and said AIW delay is about 300 ms.

5. The dual chamber pacemaker as described in claim 1, wherein said refractory interval comprises a blanking period (PVAB).

6. A method of safe atrial pacing with a dual chamber pacemaker, comprising:
sensing signals in the atrium and ventricle of a patient's heart;
defining an atrial escape interval and defining an AV interval to be initiated at the end of said atrial escape interval;
delivering atrial and ventricular pacing pulses at the expirations of said atrial escape interval and said AV interval, respectively, in the absence of sensed signals in the atrium and ventricle;
timing refractory periods (PVARP's) following ventricular pacing pulses;
detecting early atrial signals (ASR's) occurring within said PVARP's;
initiating a delay (AIW) upon occurrence of any ASR, and inhibiting delivery of an atrial pacing pulse during said AIW;
delivering a safe atrial pacing pulse (SAP) at the conclusion of said AIW; and
following delivery of said safe atrial pacing pulse, delivering a ventricular pacing pulse at the later to expire of a first time interval equal to the said AIW plus a predetermined minimum interval and a second time interval equal to said atrial escape interval plus said AV interval.

7. The method as described in claim 6, comprising detecting when a second atrial sense occurs within said AIW and said PVARP, and extending said AIW by initiating a second delay upon such determination.

8. The method as described in claim 7, wherein said step of extending said AIW comprises extending said AIW for a second delay equal to the original duration of said AIW.

9. A dual chamber pacemaker having atrial sense means for sensing natural beats from a patient's atrium, atrial generator means for generating atrial pace pulses to be delivered to the patient's atrium, ventricular sense means for sensing natural beats from said patient's ventricle, ventricular generator means for generating ventricular pace pulses to be delivered to the patient's ventricle, PVARP means for timing a refractory period PVARP following a ventricular pace pulse, and pace control means connected to receive signals from said atrial sense means and said ventricular sense means for controlling generation of pace pulses by atrial and ventricular generator means, said pace control means having VA means for timing an atrial escape interval following a ventricular pace pulse and PAV means for timing a PAV interval following delivery of an atrial pace pulse at the end of said atrial escape interval, further comprising
ASR means for detecting an early atrial sense (ASR) during said PVARP and for controlling the pacemaker response to said ASR, said ASR means further having
1. delay means for timing a delay (AIW) from the time of said ASR, means for determining whether said AIW or said atrial escape interval expires first, SAP means for controlling said atrial generator means to generate a delayed safe atrial pace stimulus (SAP) at the end of said AIW when said AIW expires after said atrial escape interval, and
2. ventricular control means for controlling generation of a ventricular pace stimulus in synchronous relation to said SAP and delayed from said SAP by a predetermined delay when said AIW expires less than said predetermined delay prior to the expiration of a time interval equal to said PAV interval, initiated at expiration of said atrial escape interval.

10. The pacemaker as described in claim 9, wherein said pacemaker is a DDDR pacemaker.

11. The pacemaker as described in claim 9, wherein said pacemaker is a DDIR pacemaker.

12. The pacemaker as described in claim 9, wherein said pacemaker is a DDI pacemaker.

13. The pacemaker as described in claim 9, wherein said pacemaker is a DDD pacemaker.

14. The pacemaker as described in claim 9, wherein said ASR means comprises means for inhibiting delivery of an AP by said atrial generator until said AIW has ended.

15. A cardiac pacemaker, comprising:
an atrial pulse generator;
a ventricular pulse generator;
an atrial sense amplifier responsive to atrial signals;
a ventricular sense amplifier responsive to ventricular signals;
timing means for defining atrial and ventricular escape intervals and for triggering said atrial pulse generator and said ventricular pulse generator to generate pacing pulses at the times of the expirations of said atrial and ventricular escape intervals, respectively;
means for defining an early atrial sense period following a ventricular depolarization sensed by said ventricular sense amplifier and for determining when an atrial depolarization has been sensed by said atrial amplifier within said early atrial sense period;
control means for defining a first interval initiated at the occurrence of an atrial depolarization sensed within said early atrial sense period and for preventing triggering of said atrial pulse generator during said first interval;
means for triggering delivery of said atrial pulse generator at the expiration of said first interval;
means for defining a second interval; and
means for triggering said ventricular pulse generator at the expiration of said ventricular escape interval if said first interval expires more than a said second interval prior to the expiration of said ventricular escape interval and for otherwise triggering said ventricular pulse generator a said second interval following expiration of said first interval.

16. A cardiac pacemaker, comprising:
an atrial pulse generator;
a ventricular pulse generator;
an atrial sense amplifier responsive to atrial signals;
a ventricular sense amplifier responsive to ventricular signals;
timing means for defining atrial and ventricular escape intervals and for triggering said atrial pulse generator and said ventricular pulse generator to generate pacing pulses at the times of the expirations of said atrial and ventricular escape intervals, respectively;
means for defining an early atrial sense period following triggering of said ventricular pulse generator and for determining when an atrial depolarization has been sensed by said atrial amplifier within said early atrial sense period;
control means for defining a first interval initiated at the occurrence of an atrial depolarization sensed within said early atrial sense period and for preventing triggering of said atrial pulse generator during said first interval;
means for triggering delivery of said atrial pulse generator at the expiration of said first interval;
means for defining a second interval; and
means for triggering said ventricular pulse generator at the expiration of said ventricular escape interval if said first interval expires more than a said second interval prior to the expiration of said ventricular escape interval and for otherwise triggering said ventricular pulse generator a said second interval following expiration of said first interval.

17. A cardiac pacemaker according to claim 15 or claim 16, further comprising means for measuring a physiologic parameter and means for varying the duration of said atrial escape interval as a function of said physiologic parameter.

18. A cardiac pacemaker according to claim 15 or claim 16, wherein said control means further comprises means responsive to a sensed atrial depolarization during said first interval, for extending said first interval.

19. A method of pacing the heart, comprising:
sensing atrial and ventricular depolarizations;
timing atrial and ventricular escape intervals and delivering atrial and ventricular pacing pulses at the times of the expirations of said atrial and ventricular escape intervals, respectively;
defining an early atrial sense period following a sensed ventricular depolarization and determining when an atrial depolarization has been sensed within said early atrial sense period;
defining a first interval initiated at the occurrence of an atrial depolarization sensed within said early atrial sense period and determining whether the time of expiration of a said atrial escape interval occurs within said first interval and preventing triggering of said atrial pulse generator at the expiration of said atrial escape interval; and
triggering delivery of said atrial pulse generator at the expiration of said first interval;
defining a second interval; and
triggering said ventricular pulse generator at the expiration of said ventricular escape interval if said first interval expires more than a said second interval prior to the expiration of said ventricular escape interval and otherwise triggering said ventricular pulse generator a said second interval following expiration of said first interval.

20. A method of pacing the heart, comprising:
sensing atrial and ventricular depolarizations;
timing atrial and ventricular escape intervals and delivering atrial and ventricular pacing pulses at the times of the expirations of said atrial and ventricular escape intervals, respectively;
defining an early atrial sense period following delivery of a said ventricular pacing pulse and determining when an atrial depolarization has been sensed within said early atrial sense period;
defining a first interval initiated at the occurrence of an atrial depolarization sensed within said early atrial sense period and determining whether the time of expiration of a said atrial escape interval occurs within said first interval and preventing triggering of said atrial pulse generator at the expiration of said atrial escape interval; and
triggering delivery of said atrial pulse generator at the expiration of said first interval;
defining a second interval; and
triggering said ventricular pulse generator at the expiration of said ventricular escape interval if said first interval expires more than a said second interval prior to the expiration of said ventricular escape interval and otherwise triggering said ventricular pulse generator a said second interval following expiration of said first interval.

21. A method according to claim 19 or claim 20, further comprising measuring a physiologic parameter and varying the duration of said atrial escape interval as a function of said physiologic parameter.

22. A cardiac pacemaker according to claim 19 or claim 20, further comprising responding to a sensed atrial depolarization during said first interval by extending said first interval.

* * * * *